US012125591B2

(12) United States Patent
Rendschmidt et al.

(10) Patent No.: US 12,125,591 B2
(45) Date of Patent: Oct. 22, 2024

(54) METHOD FOR ADJUSTING A BOLUS AMOUNT OF INSULIN, DEVICE AND MEDICAL SYSTEM

(71) Applicant: Roche Diabetes Care, Inc., Indianapolis, IN (US)

(72) Inventors: Til Rendschmidt, Wiesbaden (DE); Itzhak Grinberg, Haifa (IL); Wiebke Mueller-Hoffmann, Mannheim (DE); Andreas Schmitz, Wilhelmsfeld (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 723 days.

(21) Appl. No.: 16/862,643

(22) Filed: Apr. 30, 2020

(65) Prior Publication Data

US 2020/0253515 A1  Aug. 13, 2020

Related U.S. Application Data

(63) Continuation of application No. PCT/EP2018/080400, filed on Nov. 7, 2018.

(30) Foreign Application Priority Data

Nov. 8, 2017 (EP) .................................. 17200590

(51) Int. Cl.
*G16H 50/20* (2018.01)
*A61B 5/00* (2006.01)
(Continued)

(52) U.S. Cl.
CPC ............ *G16H 50/20* (2018.01); *A61B 5/0013* (2013.01); *A61B 5/743* (2013.01); *G16H 10/60* (2018.01);
(Continued)

(58) Field of Classification Search
CPC ........ G16H 50/20; G16H 10/60; G16H 20/17; G16H 20/60; A61B 5/0013; A61B 5/743;
(Continued)

(56) References Cited

U.S. PATENT DOCUMENTS

2003/0114836 A1   6/2003  Estes et al.
2005/0245904 A1*  11/2005  Estes ................. A61M 5/14244
                                                      604/890.1
(Continued)

FOREIGN PATENT DOCUMENTS

EP       1102194 A2    5/2001
WO   WO 2008/048586 A1    4/2008

OTHER PUBLICATIONS

International Search Report and Written Opinion of the International Searching Authority, PCT/EP2018/080400, Feb. 20, 2019, 15 pages.

*Primary Examiner* — Eliza A Lam
(74) *Attorney, Agent, or Firm* — Bose McKinney & Evans LLP

(57) ABSTRACT

A method for adjusting a bolus amount of insulin for a meal event using a control unit having a processing unit and a touch screen display as well as a medical control device and a medical system configured to perform the method. Additionally, the present disclosure relates to a computer program or computer program product that, when executed, performs the method. A carbohydrate-based bolus amount of insulin can be delivered in a first bolus and a second bolus. A movable slider displayed on the touch screen display can be used to adjust the relative amounts of the first and second boli.

15 Claims, 6 Drawing Sheets

(51) Int. Cl.
*A61B 5/145* (2006.01)
*A61K 38/28* (2006.01)
*G16H 10/60* (2018.01)
*G16H 20/17* (2018.01)
*G16H 20/60* (2018.01)

(52) U.S. Cl.
CPC ............. *G16H 20/17* (2018.01); *G16H 20/60* (2018.01); *A61B 5/14532* (2013.01); *A61K 38/28* (2013.01)

(58) Field of Classification Search
CPC ........ A61B 5/14532; A61B 2560/0431; A61B 2560/0456; A61B 2560/0475; A61B 5/0077; A61B 5/6898; A61B 5/4839; A61K 38/28; A61M 5/14248; A61M 2205/3303; A61M 2205/3523; A61M 2205/3584; A61M 2205/3592; A61M 2205/50; A61M 2205/505; A61M 5/1723
See application file for complete search history.

(56) References Cited

U.S. PATENT DOCUMENTS

| | | | |
|---|---|---|---|
| 2009/0254037 A1* | 10/2009 | Bryant, Jr | A61M 5/16886 700/282 |
| 2010/0249530 A1* | 9/2010 | Rankers | A61B 5/14532 600/300 |
| 2010/0286653 A1* | 11/2010 | Kubel | A61M 5/142 434/262 |
| 2012/0232485 A1* | 9/2012 | Blomquist | G16H 40/63 604/151 |
| 2013/0141438 A1 | 6/2013 | Neftel | |
| 2014/0058749 A1 | 2/2014 | Galley et al. | |
| 2015/0011970 A1* | 1/2015 | Kamen | G16H 10/65 604/151 |

* cited by examiner

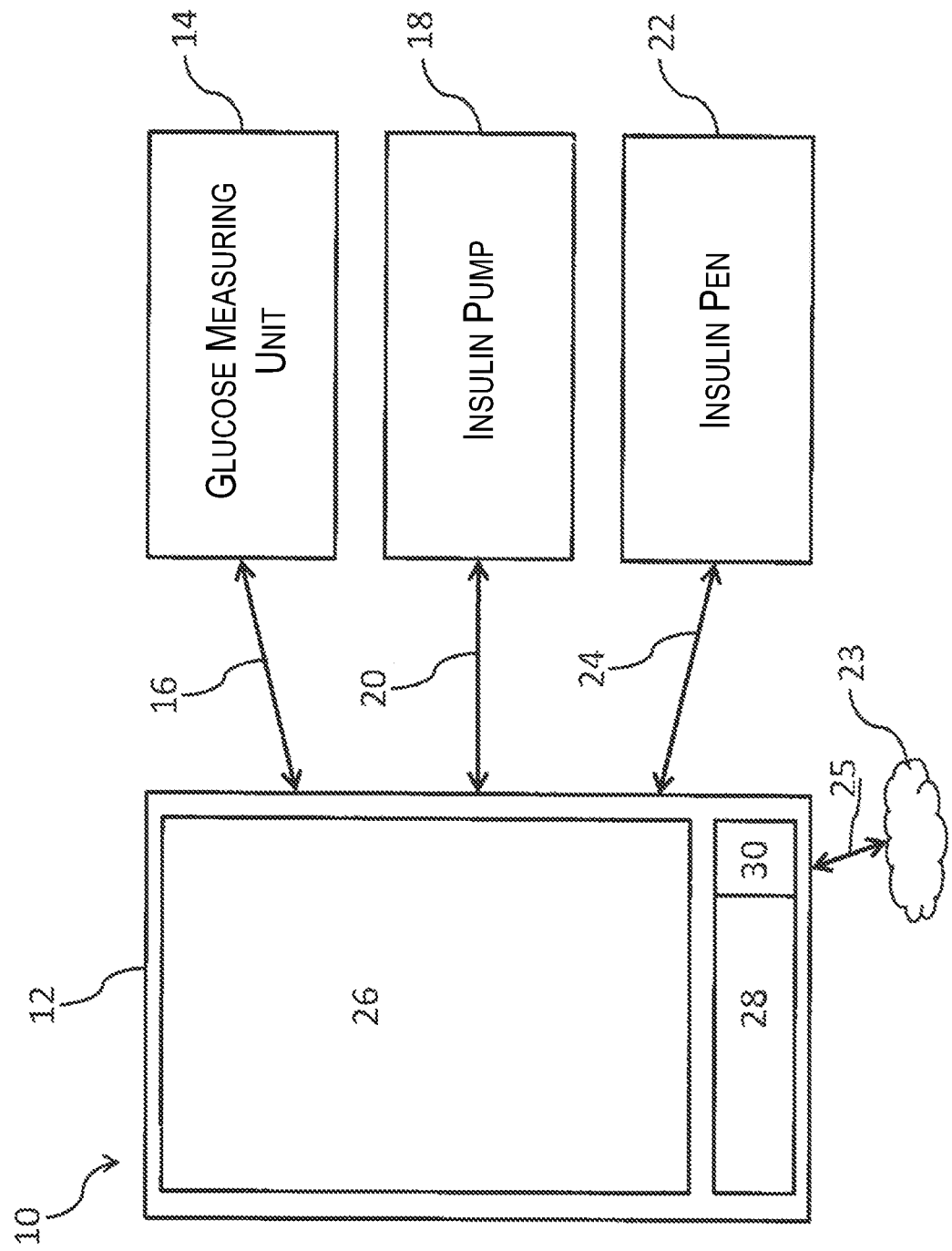

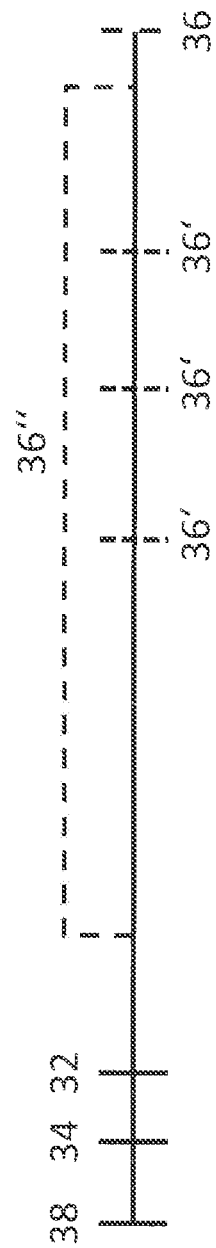

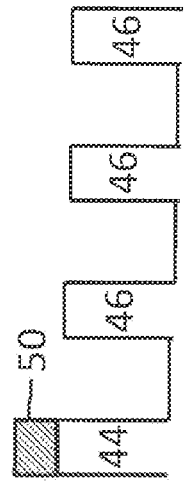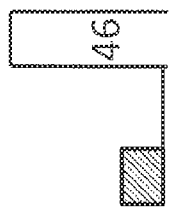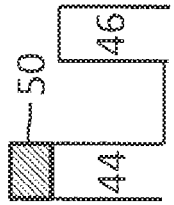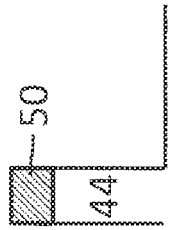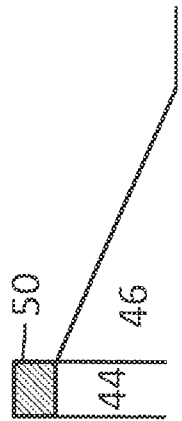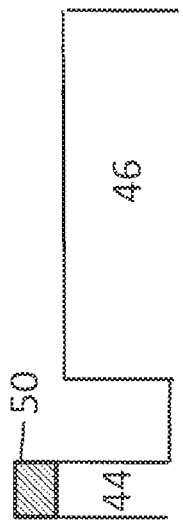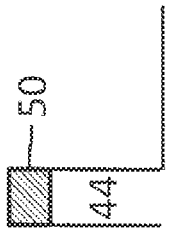

METHOD FOR ADJUSTING A BOLUS AMOUNT OF INSULIN, DEVICE AND MEDICAL SYSTEM

RELATED APPLICATIONS

This application is a continuation of PCT/EP2018/080400, filed Nov. 7, 2018, which claims priority to EP 17 200 590.2, filed Nov. 8, 2017, both of which are incorporated herein by reference in their entirety.

BACKGROUND

The present disclosure refers to a method for adjusting a bolus amount of insulin for a meal event using a control unit having a processor and a touch screen display as well as a medical control device and a medical system configured to perform the method. Additionally, the present disclosure refers to a computer program or computer program product that, when executed, performs the method.

Diabetes mellitus is a group of chronic metabolic disorders characterized by raised blood glucose levels and impaired carbohydrate, fat, and protein metabolism. The insulin deficiency responsible for this disorder results from a defect in insulin secretion or the effect of insulin on the organism. Absolute insulin deficiency—which occurs in type I diabetes—is usually caused by an auto-immunological destruction of insulin-producing beta cells in the pancreas. These patients must rely on exogenous sources of insulin. Individuals with type II diabetes are resistant to insulin and suffer from impaired insulin secretion. Both of these disorders can occur to varying degrees. The exact causes of this disease are not known. Treatment of relative insulin deficiency ranges from dietary modifications and oral anti-diabetics to exogenous insulin administration.

Patients who suffer from Diabetes mellitus over the long term and, therefore, have chronic hyperglycemia, develop organ damage, impairment, and even failure. The eyes, kidneys, nerves, blood vessels, and the heart are affected in particular. Prevention of these late complications is the main goal of diabetes therapy. In the most commonly used therapy today, patients are administered slow-acting insulin that covers the basal insulin demand. They are also administered a bolus of normal insulin or a fast-acting insulin to offset the carbohydrates consumed during a meal.

In the art, different approaches to determine a bolus amount of insulin in connection with a meal event are known. US 2013/141438 A1 proposes to resolve problems at the level of the risk of error in the inputting of data on a programming screen. US 2013/141438 A1 generally discloses a system for inputting and displaying data comprising a programming screen, data input means and means for displaying said data on said screen. The system also comprises a series of indicators and means for activating said indicators which are adapted so as to activate and associate a specific indicator for each type of data to be input.

Document US 2014/058749 A1 describes a method for presenting a GUI for modifying medical data on a handheld medical device is disclosed. The method includes determining a correction bolus amount and a meal bolus amount for the patient. The method also includes presenting the GUI on a display of the medical device and presenting the correction bolus amount, the meal bolus amount and a total bolus amount in the GUI. The method also includes presenting a correction bolus amount modification field and a meal bolus amount field in the GUI. The correction bolus amount modification field and the meal bolus amount modification field allow the patient to provide input to modify the correction bolus amount and meal bolus amount, respectively. The method further includes receiving the input and generating an advice history record based on the input.

In document US 2012/232485 A1 methods of regulating blood glucose using an insulin pump are disclosed. A method includes storing a target blood glucose level in the pump. The method also includes receiving a current blood glucose level, and comparing the current blood glucose level to the target blood glucose level. The method further includes, upon detection of a current blood glucose level lower than the target blood glucose level, calculating a carbohydrate value required to change the current blood glucose level to the target blood glucose level.

Document US2010/249530 A1 relates to a method of providing bolus dosage recommendations for diabetics that includes receiving an image of a meal to be consumed by a user. The image is analyzed to identify at least one food item in the image. A bolus dosage recommendation is calculated based on the identified at least one food item in the image.

SUMMARY

The present disclosure teaches a method, a device, a system and a computer program product for safe adjustment or setting of a bolus amount of insulin for a meal event. Additionally, a method, a device, a system and a computer program product are provided for accurate and reliable bolus adjustment, supporting the user in reaching enhanced therapy results. Further, a method, a device, a system and a computer program product that aid and simplify the use of complex bolus delivery schemes are provided.

This disclosure relates to a method for adjusting a bolus amount of insulin for or on a meal event using a control unit having a processor and a touch screen display, the method comprising the steps:

receiving, by the processor, a carbohydrate amount associated with the meal event and determining a carbohydrate-based bolus amount of insulin;

outputting on the touch screen display a slider movable via touch screen gestures, wherein the processor determines, based on the position of the slider, a first bolus amount of insulin to be delivered immediately and/or a second bolus amount of insulin to be delivered at a later point in time, wherein the first bolus amount of insulin and/or the second bolus amount of insulin add up to a carbohydrate-based bolus amount of insulin and wherein the first bolus amount or the second bolus amount may be zero;

outputting on the touch screen display a total meal bolus amount of insulin including the carbohydrate-based bolus amount of insulin and/or a correction bolus, further outputting on the touch screen display the correction bolus, the first bolus amount of insulin to be delivered immediately, as determined by the position of the slider and a second bolus amount of insulin to be delivered at a later point in time as determined by the position of the slider.

A meal event as used herein signifies a meal intake or an occurrence at which a patient with diabetes eats a meal. The meal may include one meal item or various meal items. The meal event may be characterized by time, size, ingredients and/or nutrient content information. In particular, the meal event may be characterized by the carbohydrate content or carbohydrate amount and/or further nutrient content information. Nutrient content information may include any other ingredient present in the meal, particularly a fat content, a protein content, a fiber content and/or a glycemic index.

Determining a carbohydrate-based bolus amount of insulin includes any determination that relates the carbohydrates included in the meal with the corresponding bolus amount of insulin. Such methods are based on modelling the carbohydrate effect on a glucose level and the corresponding insulin dose effect on the glucose level such that a patient's glycemic state ends up in a target range after the meal event. Such methods are, for instance, described in EP1102194A2, which is hereby incorporated by reference. In one embodiment, the insulin dose taking effect in a certain time interval and the portion of carbohydrates consumed that take effect in the certain time interval may be used to determine an extrapolated glucose concentration at the end of the certain time interval based on a glucose level measured at the beginning of the certain time interval. The method may further include factors like the patient's insulin sensitivity, empirical factors, such as offsets or weighting factors, insulin on board and/or the patient's basal insulin demand over 24 hours.

The carbohydrate-based bolus amount of insulin may be determined according to an insulin delivery scheme including amount and timing of the bolus parts. Such an insulin delivery scheme may include a bolus amount to be delivered immediately or to be delivered at a later point in time or both. For example, the insulin delivery scheme may only comprise the first bolus amount of insulin to be delivered immediately. In another example, the insulin delivery scheme may only comprise the second bolus amount of insulin to be delivered at a later point in time, e.g., after an immediate bolus amount, such as a correction bolus. In a further alternative, the insulin delivery scheme may comprise both the first bolus amount of insulin to be delivered immediately and the second bolus amount of insulin to be delivered at a later point in time, e.g., after the first bolus amount. Such a scheme is also known as a dual, multiple or extended bolus. Herein, a dual bolus refers to the first bolus amount of insulin to be delivered immediately and to one second bolus amount of insulin to be delivered at one later point in time. Multiple bolus refers to the first bolus amount of insulin to be delivered immediately and to more than one discrete part(s) of the second bolus amount of insulin to be delivered at more than one later points in time. Extended bolus refers to the first bolus amount of insulin to be delivered immediately and to the second bolus amount of insulin to be delivered continuously over a time range. The second bolus amount of insulin to be delivered continuously over a time range can be started either directly or with a delay after the first bolus amount of insulin to be delivered immediately. The timing of the delivery scheme may be set by the user. Alternative delivery scheme timings may be determined by the processor of the control unit based on predefined delivery scheme timings stored in a storage unit, or the delivery scheme timings may be determined based on, e.g., the glucose level, the carbohydrate amount and/or nutrient meal content information.

In one embodiment, device settings may be provided including delivery schemes for insulin pump devices and pen devices. Here, delivery schemes for insulin pumps may include the carbohydrate-based bolus amount of insulin to be determined according to an insulin delivery scheme with the second bolus amount of insulin to be delivered continuously over a time range. Delivery schemes for insulin pens may include the carbohydrate-based bolus amount of insulin to be determined according to an insulin delivery scheme with the second bolus amount to be delivered in one or more discrete parts at one or more discrete point(s) in time after the first bolus amount or after the meal event. Such device settings may be set manually by the user or automatically by detecting which type of device the control unit is connected to.

The first bolus amount of insulin to be delivered immediately may include any bolus amount that is to be delivered either on the meal event or in a time window before or after a meal event that is smaller than the time window of the second bolus amount of insulin to be delivered at a later point in time. Such a time window is preferably ≤30 min (minutes), most preferred ≤15 min and particularly preferred ≤5 min or between 1 and 4 min.

The second bolus amount of insulin to be delivered at a later point in time may include any bolus amount that is to be delivered in a time window after a meal event that is larger than the time window for the immediate bolus amount. Such a time window is preferably ≥30 min, most preferred ≥1 h (hour) and particularly preferred ≥1.5 h (hour) or between 1 h and 5 h.

The correction bolus includes any bolus amount that relates to the measured glucose level, preferably before a meal event. The correction bolus may relate to a bolus amount of insulin to correct for glucose levels that lie above the target range. In particular, the correction bolus may relate to a bolus amount of insulin to correct for a hyperglycemic state. The target range may have an upper and a lower limit and lie, for instance, in the range of 70 mg/dl and 180 mg/dl. A hyperglycemic state may comprise any glycemic state above the upper limit of the target range and may lie, for instance, in a range above 180 mg/dl. A hypoglycemic state may comprise any glycemic state below the lower limit of the target range and may lie, for instance, in a range below 70 mg/dl.

The total meal bolus amount preferably includes the carbohydrate-based bolus amount of insulin and/or the correction bolus. Depending on the delivery scheme the total meal bolus amount may include a fraction of one or more types of bolus amount(s) of the delivery scheme. Hence, the total meal bolus amount may comprise the sum of the carbohydrate-based bolus amount of insulin and the correction bolus. In another alternative, the total meal bolus amount may comprise only one, namely, only the first bolus amount of insulin or the second bolus amount of insulin. In yet another alternative, the total meal bolus amount may comprise any of the above, namely, the correction bolus and the carbohydrate-based bolus amount of insulin, which may further include the first bolus amount of insulin and/or the second bolus amount of insulin.

The step of outputting on the touch screen display the first bolus amount of insulin to be delivered immediately, as determined by the position of the slider, and a second bolus amount of insulin to be delivered at a later point in time, as determined by the position of the slider, includes, when the position of the slider is changed by user interaction or by finger gestures moving the slider, updating the first bolus amount of insulin to be delivered immediately and the second bolus amount of insulin to be delivered at a later point in time. The updated first bolus amount of insulin to be delivered immediately and second bolus amount of insulin to be delivered at a later point in time are instantly updated and the corresponding outputs are displayed. Here, instantly may be understood in the sense that minimum visible delay is present on the touch screen display device as caused by processing times.

The method may further comprise the step of receiving, by the control unit, a glucose level measured via a glucose measuring unit prior to the meal event, providing the measured glucose level to the processor and determining, by the processor, a correction bolus based on the glucose level measured prior to the meal event, wherein the correction bolus, the first bolus amount of insulin and the second bolus amount of insulin add up to a total meal amount of insulin.

The correction bolus may be used to bring the patient's glucose level back into the target range before the meal event. The correction bolus may be an amount of insulin to be delivered immediately together with the first bolus amount of insulin based on the carbohydrate amount. The glucose level measured prior to the meal event is preferably measured in a time range of, e.g., ≤30 min, ≤20 min or ≤10 min before the meal event takes place. Based on the measured glucose level, the correction bolus is calculated by using, for example, the patient's insulin sensitivity and the insulin effectiveness profile.

The step of outputting on the touch screen display may further comprise outputting the correction bolus, wherein the correction bolus is independent of the position of the slider. In such an embodiment, the output on the touch screen display includes updating only the first bolus amount of insulin and the second bolus amount of insulin, when the position of the slider is changed by user interaction or finger gestures, and leaving the correction bolus at a fixed amount associated with the first amount of insulin to be delivered immediately.

The touch screen may include sensors, such as capacitive sensors, for detecting finger gestures along a slider path reaching from a first slider position to a second slider position, wherein the first slider position is associated with the carbohydrate-based bolus amount of insulin being the first bolus amount of insulin to be delivered immediately and the second slider position is associated with the carbohydrate-based bolus amount of insulin being the second bolus amount of insulin to be delivered at a later point in time. In particular, the first and the second slider positions are end positions of the slider path. Preferably the slider path is a straight path from one side, e.g., the left side, of the touch screen display to a second side, e.g., the right side, of the touch screen display.

A slider position between the first slider position and the second slider position may be associated with the first bolus amount of insulin to be delivered immediately and the second bolus amount of insulin to be delivered at a later point in time, wherein the partitioning between first and second bolus amount of insulin is determined based on the partitioning of the slider path with the slider position between the first slider position and the second slider position. In a further embodiment, the correction bolus is independent of the partitioning of the slider path with the slider position between the first slider position and the second slider position.

The first bolus amount of insulin to be delivered immediately and a second bolus amount of insulin to be delivered at a later point in time may be arranged on the touch screen display in connection with the slider. Preferably, the first bolus amount of insulin is displayed in close vicinity of the first slider position and the second bolus amount of insulin is displayed in close vicinity of the second slider position. Further preferably, the correction bolus is displayed in close vicinity of the first slider position in connection with the first bolus amount of insulin. Further preferred, the correction bolus is displayed as separate item, e.g., separate from the first bolus amount of insulin, in the vicinity of the first slider position. In yet a further preferred embodiment, the display includes numerical numbers or percentages. In such an embodiment, the total meal bolus amount and the correction bolus may be displayed as numbers and the first and second bolus amount adjustable via the slider may be displayed in percentages.

Nutrient meal content information associated with the meal event may be received by the processor. In one example, the carbohydrate amount and/or further nutrient meal content information is determined via a food data base, e.g., stored on a cloud sever or stored directly in storage unit of the control unit, including an estimated carbohydrate amount and/or further nutrient meal content information for specific meals or meal items. In a further example, the carbohydrate amount and/or further nutrient meal content information is determined by photographic reconstruction routines based on a photographic image of the meal or meal items provided by a camera unit of the control unit. In such an example, the routine may include taking a photograph, detecting meal item(s) by type, segmenting the photograph according to the detected meal item(s), estimating the size and the nutrient content of the meal item(s) based on the segmented photograph.

On outputting the slider, the displayed position of the slider may be pre-set based on the provided carbohydrate amount and/or further nutrient meal content information. Such pre-setting may result from the estimation of the carbohydrate amount and/or further nutrient meal content information via a food data base or photographic reconstruction routines. Such estimation may be used to determine the carbohydrate-based bolus amount, including first and second bolus amount and the respective delivery scheme timings.

In a further embodiment, the total meal bolus amount of insulin and the delivery scheme are communicated or sent via a communication unit to an insulin delivery system such as an insulin pump or an insulin pen. Here, the delivery scheme may include the carbohydrate-based bolus amount of insulin with the first bolus amount of insulin to be delivered immediately, as determined by the position of the slider, and the second bolus amount of insulin to be delivered at a later point in time, as determined by the position of the slider, and/or the correction bolus. Communication or sending may be triggered automatically by the medical control device, the control unit, the communication unit or the processor, e.g., through a spot monitoring measurement signifying the glucose level at a single point in time or, e.g., whenever a bolus amount of insulin is determined by the medical control device. In alternative embodiments, communication or sending may be triggered by the medical control device, the control unit, the communication unit or the processor manually by the patient via a patient input, particularly via patient confirmation input.

Additionally, this disclosure relates to a medical control device for adjusting a bolus amount of insulin on or for a meal event including a control unit having a processor and a touch screen display, wherein the system includes:
  a processor to receive a carbohydrate amount associated with the meal event and to determine a carbohydrate-based bolus amount of insulin;
  a touch screen display to output a slider movable via touch screen gestures, wherein the processor determines, based on the position of the slider, a first bolus amount of insulin to be delivered immediately and/or a second bolus amount of insulin to be delivered at a later point in time, wherein the first bolus amount of insulin and the second bolus amount of insulin add up to a carbohydrate-based bolus amount of insulin,
  the touch screen display further displays a total meal bolus amount of insulin including the carbohydrate-based bolus amount of insulin and/or a correction bolus, and further displays the correction bolus, the first bolus amount of insulin to be delivered immediately and a second bolus amount of insulin to be delivered at a later point in time.

The medical control device may be configured to perform the method for adjusting a bolus amount of insulin for a meal event as disclosed above. In particular, the medical control device comprises a control unit having a processor and a touch screen display and is, preferably, configured to perform the method comprising the steps:

receiving, by the processor, a carbohydrate amount associated with the meal event and determining a carbohydrate-based bolus amount of insulin;

outputting on the touch screen display a slider movable via touch screen gestures, wherein the processor determines, based on the position of the slider, a first bolus amount of insulin to be delivered immediately and/or a second bolus amount of insulin to be delivered at a later point in time, wherein the first bolus amount of insulin and/or the second bolus amount of insulin add up to a carbohydrate-based bolus amount of insulin;

outputting on the touch screen display a total meal bolus amount of insulin, including the carbohydrate-based bolus amount of insulin and/or a correction bolus, outputting on the touch screen display the correction bolus, the first bolus amount of insulin to be delivered immediately, as determined by the position of the slider, and a second bolus amount of insulin to be delivered at a later point in time, as determined by the position of the slider.

Furthermore, the medical control device or elements of the medical control device, such as the control unit having a processor and a touch screen display, are preferably configured to perform any method step or any combination of method steps disclosed above in connection with the method for adjusting a bolus amount of insulin for a meal event.

In one embodiment, the control unit further includes a data communication unit for communication with at least one medical device and/or a cloud server. In a further embodiment, the control unit is configured to receive a glucose level measured via a glucose measuring unit prior to the meal event, to provide the measured glucose level to the processor and the processor is configured to determine a correction bolus based on the glucose level measured prior to the meal event, wherein the correction bolus, the first bolus amount of insulin and the second bolus amount of insulin add up to a total meal amount of insulin.

In a further embodiment, the control unit is configured to communicate the total meal amount of insulin, the first bolus amount of insulin and the second bolus amount of insulin to an insulin delivery system. Additional information relating to the delivery scheme may also be communicated.

Further, this disclosure relates to a medical system including the medical control device, as set out above, in communication with a glucose measuring unit and/or an insulin delivery system.

Preferably, the medical system is configured to perform the method for adjusting a bolus amount of insulin for a meal event, as disclosed above. In particular, the medical system comprises medical control device including a control unit having a processor and a touch screen display and is preferably configured to perform the method comprising the steps:

receiving, by the processor, a carbohydrate amount associated with the meal event and determining a carbohydrate-based bolus amount of insulin;

outputting on the touch screen display a slider movable via touch screen gestures, wherein the processor determines, based on the position of the slider, a first bolus amount of insulin to be delivered immediately and/or a second bolus amount of insulin to be delivered at a later point in time, wherein the first bolus amount of insulin and/or the second bolus amount of insulin add up to a carbohydrate-based bolus amount of insulin;

outputting on the touch screen display a total meal bolus amount of insulin, including the carbohydrate-based bolus amount of insulin and/or a correction bolus, outputting on the touch screen display the correction bolus, the first bolus amount of insulin to be delivered immediately, as determined by the position of the slider, and the second bolus amount of insulin to be delivered at a later point in time, as determined by the position of the slider.

Furthermore, the medical system or elements of the medical system, such as the medical control device including the control unit having a processor and a touch screen display, are preferably configured to perform any method step or any combination of method steps disclosed above in connection with the method for adjusting a bolus amount of insulin for a meal event.

Further, a computer program and a computer program product having program code means for executing the method for adjusting a bolus amount of insulin for or on a meal event are also disclosed.

The method for adjusting a bolus amount of insulin for or on a meal event, as disclosed above, is preferably implemented as a computer program on a medical control device of a medical system. Other approaches, of course, are also suitable. For this purpose, the computer program may be stored with the aid of a storage unit (for example, ROM, EEPROM, or the like) of the medical control device. The method for adjusting a bolus amount of insulin for a meal event is executed by processing on the medical control device. The medical control device may have a processor comprising a microprocessor, a programmable integrated circuit (field-programmable gate array (FPGA)), an application-specific integrated circuit (ASIC), a digital signal processor (DSP), or the like. The computer program may be stored on a non-transient computer-readable data carrier (diskette, CD, DVD, hard drive, USB memory stick, memory card, or the like) or on an internet or cloud server as a computer program product, and from there transferred into the storage unit of the medical control device.

Further, this disclosure relates to a non-transitory computer-readable data storage medium storing a computer program having program codes which, when executed on a processor of a medical control device of a medical system, performs the method for adjusting a bolus amount of insulin for a meal event as disclosed above, the method comprising the steps of:

receiving, by the processor, a carbohydrate amount associated with the meal event and determining a carbohydrate-based bolus amount of insulin;

outputting on the touch screen display a slider movable via touch screen gestures, wherein the processor determines, based on the position of the slider, a first bolus amount of insulin to be delivered immediately and/or a second bolus amount of insulin to be delivered at a later point in time, wherein the first bolus amount of insulin and/or the second bolus amount of insulin add up to a carbohydrate-based bolus amount of insulin;

outputting on the touch screen display a total meal bolus amount of insulin, including the carbohydrate-based bolus amount of insulin and/or a correction bolus, further outputting on the touch screen display the correction bolus, the first bolus amount of insulin to be delivered immediately, as determined by the position of the slider, and the second bolus amount of insulin to be delivered at a later point in time, as determined by the position of the slider.

Furthermore, the non-transitory computer-readable data storage medium storing a computer program having program codes which, when executed on a processor of a medical control device of a medical system, performs preferably any method step or any combination of method steps disclosed above in connection with the method for adjusting a bolus amount of insulin for a meal event.

The various features described herein may be realized in an isolated fashion as well as in alternative combinations, as the skilled person will recognize.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIG. 1 shows an exemplary embodiment of a medical system including a medical control device in communication with a glucose measuring unit, an insulin pump and an insulin pen.

FIG. 2 shows one example of a time line with a number of events around a meal event.

FIGS. 6a-6d and FIGS. 7a-7c show exemplary embodiments for insulin pump and insulin pen based delivery schemes.

Figure 3A:
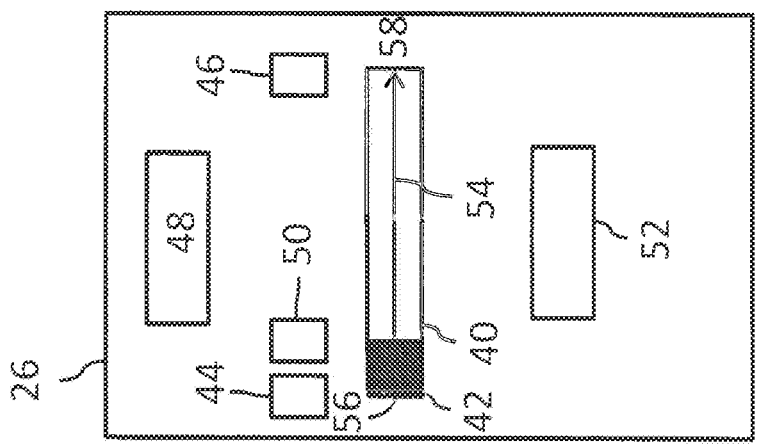
FIGS. 3a-3c show an exemplary embodiment of a medical control device with a touch screen display for outputting a slider for insulin adjustment.

The embodiments are schematically depicted in the Figures. Identical references numbers in these figures refer to identical or functionally comparable elements. The embodiments described below are not intended to be exhaustive or to limit the invention to the precise forms disclosed. Rather, the embodiments are chosen and described so that others skilled in the art may appreciate and understand the principles and practices of this disclosure.

DESCRIPTION

FIG. 1 shows an exemplary embodiment of a medical system 10, including a medical control device (also referred to herein as "control unit") 12 in communication 16, 20, 24 with the glucose measuring unit 14, the insulin pump 18, such as a patch pump directly worn on the body, or the insulin pen 22, such as a smart insulin pen. The medical control device 12 may be a smartphone or mobile phone. The smartphone refers to a multifunctional mobile phone including a camera, a network browser, a mail function, and the like as well as the functions of a mobile phone. The medical control device 12 is not limited to a smartphone and may be any other suitable device such as a PDA, a PC or a remote control. The medical control device 12 includes a control unit with a processor or processing unit 28 and a touch screen display 26.

The communication between the medical control device 12 and the other devices 14, 18, 22 of the medical system 12 or a cloud server 23 is established via a communication unit 28 providing for communication with such devices 14, 18, 22, 25 via, e.g., a Bluetooth LE™, an NFC or a WLAN unit, which performs communication using a designated protocol. Similarly the glucose measuring unit 14, the insulin pump 18 or the insulin pen 22 include a corresponding communication unit, respectively, providing for communication with the medical control device 12 via, e.g., a Bluetooth LE™, an NFC or a WLAN unit, which performs communication using a designated protocol. The communication may be uni- or bidirectional depending on the data that is communicated between the devices.

The glucose measuring unit 14 may be a continuous glucose monitor, which is configured for measuring the glucose level in subcutaneous fluid. The glucose measuring unit 14 may be fully or partly implantable into subcutaneous tissue. Here, the medical control device 12 may be configured to communicate with the glucose measuring unit 14 by continuously receiving measured glucose levels. Hence, the medical control device 12 may be enabled to use the glucose level in order to adjust an amount of bolus or basal insulin depending on the current glycemic status of the patient.

The glucose measuring unit 14 may be a spot monitoring glucose meter, which is configured for measuring the glucose level in a sample of blood extracted from the patient through a lancing device. Here, the medical control device 12 may be configured to communicate with the glucose measuring unit 14 by receiving measured glucose levels, which may be automatically triggered through a spot monitoring measurement signifying the glucose level at a single point in time or manually triggered by the patient via a patient input.

The insulin pump 18 may be a patch pump, which is directly worn on the body and configured to deliver a basal and/or bolus amount of insulin to the patient. Here, the medical control device 12 may be configured to communicate with the insulin pump 18 by sending a basal and/or bolus amount of insulin to the insulin pump 18. Such sending may be automatically triggered whenever a bolus insulin amount or a change in the basal insulin amount is determined by the medical control device 12. Alternatively, such sending may be manually triggered by the patient via a patient input, such as patient confirmation input. Hence, the medical control device 12 may be enabled to control the insulin pump 18 in order to adjust an amount of bolus or basal insulin depending on the current glycemic status of the patient.

The insulin pen 22 may be a smart insulin pen, which may be configured to adjust the bolus insulin amount to be delivered to the patient. Here, the medical control device 12 may be configured to communicate with the insulin pen 22 by sending a bolus insulin amount to the insulin pen 22. Such sending may be automatically triggered whenever a bolus insulin amount is determined by the medical control device 12. Alternatively, such sending may be manually triggered by the patient via a patient input, such as patient confirmation input. Hence, the medical control device 12 may be enabled to control the insulin pen 22 in order to adjust an amount of bolus insulin depending on the current glycemic status of the patient.

FIG. 2 shows one example of a time line with a number of subsequent events around a meal event 32.

Here, the meal event 32 signifies an event at which the patient with diabetes eats a meal including one or more meal items. In one scenario, owing to the time it takes for insulin to take effect, the patient with diabetes plans a meal event 32 and the bolus amount of insulin may be adjusted prior to the meal event 32. In an exemplary scenario, the patient with diabetes may measure the glucose level, either via continuous monitoring or spot monitoring, at time point 38. Based on such a measurement, the correction bolus 50 and, based on the carbohydrate content of the planned meal event 32, the first and second bolus amount of insulin 44, 46 may be determined at time point 34.

Here, the first and second bolus amount of insulin 44, 46 may be determined to be delivered according to a delivery scheme 36, 36', 36". Such schemes include the second bolus amount of insulin 46 to be delivered at one discrete point in time 36 after the meal event 32, the second bolus amount of insulin 46 to be delivered at more than one discrete points in time 36' after the meal event 32 or the second bolus amount of insulin 46 to be delivered continuously over a period of time 36" after the meal event 32. The first bolus amount of insulin 44 and the correction bolus 50 may be determined in such schemes to be delivered immediately, for example, 15 minutes before the meal event 32.

Figure 3B:
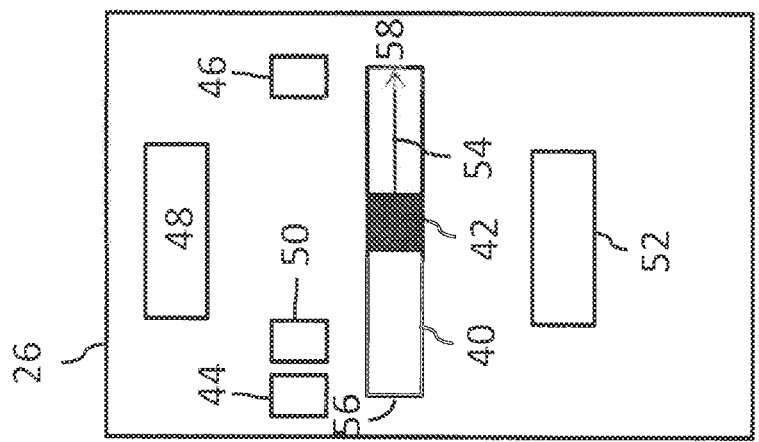
Figure 3C:
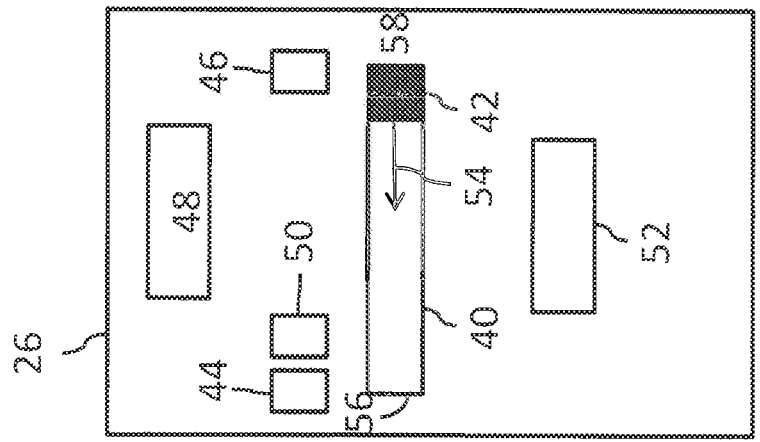

FIGS. 3a, 3b and 3c show an exemplary embodiment of a medical control device 12 with a touch screen display 26 for outputting the slider 40 for insulin adjustment.

In the method for adjusting the bolus amount of insulin for a meal event 32 using a control unit 12 having a processor 28 and a touch screen display 30, the processor 28 receives a carbohydrate amount associated with the meal event 32 and determines a carbohydrate-based bolus amount of insulin. Following such determination, a slider 40, which is movable via touch screen gestures, is output on the touch screen display 26. The processor 28 determines based on the position 42 of the slider 40 a first bolus amount of insulin 44 to be delivered immediately and/or a second bolus amount of insulin 46 to be delivered at a later point in time, wherein the first bolus amount of insulin 44 and/or the second bolus amount of insulin 46 add up to a carbohydrate-based bolus amount of insulin.

Additionally, the total meal bolus amount of insulin 48, including the carbohydrate-based bolus amount of insulin and/or the correction bolus 50, the correction bolus 50, the first bolus amount of insulin 44 to be delivered immediately, as determined by the position 42 of the slider 40, and the second bolus amount of insulin 46 to be delivered at a later point in time, as determined by the position 42 of the slider 40, are displayed on the touch screen display 26. Furthermore, additional information 52 relating to the delivery scheme of the second bolus amount of insulin 46 to be delivered at a later point in time, such as the duration of the delay for the second bolus amount of insulin 46 to be delivered at a later point in time, the partitioning of the second bolus amount of insulin 46 to be delivered at a later point in time or the profile of the second bolus amount of insulin 46 to be delivered at a later point in time, may be displayed.

The output on the touch screen display 26 of the first bolus amount of insulin 44 to be delivered immediately, as determined by the position 42 of the slider 40, and a second bolus amount of insulin 46 to be delivered at a later point in time, as determined by the position 42 of the slider 40, includes updating the first bolus amount of insulin 42 to be delivered immediately and the second bolus amount of insulin 46 to be delivered at a later point in time when the position 42 of the slider 40 is changed by user interaction or detection of finger gestures on the touch screen 26. The updated first bolus amount of insulin 42 to be delivered immediately and a second bolus amount of insulin 46 to be delivered at a later point in time are instantly updated and the corresponding outputs are numerically displayed as numbers or in percentages.

For such updating, the touch screen may include sensors, such as capacitive sensors, for detecting finger gestures along a slider path 54 reaching from a first slider end position 56 to a second slider end position 58. As shown in the exemplary embodiment of FIGS. 3a and 3c, the first slider end position 56 is associated with the carbohydrate-based bolus amount of insulin being the first bolus amount of insulin 44 to be delivered immediately and the second slider end position 58 is associated with the carbohydrate-based bolus amount of insulin being the second bolus amount of insulin 46 to be delivered at a later point in time.

Any slider position 42, as illustrated in FIG. 3b, between the first slider end position 56 and the second slider end position 58 is associated with the first bolus amount of insulin 44 to be delivered immediately and the second bolus amount of insulin 46 to be delivered at a later point in time, wherein the partitioning between first and second bolus amount of insulin 44, 46 is determined based on the partitioning of the slider path 40 with the slider position 42 between the first slider end position 56 and the second slider end position 58. Preferably, the first and second bolus amount of insulin 44, 46 are displayed in percentages.

In addition to the carbohydrate-based bolus amount of insulin, the correction bolus 50 is displayed on the touch screen display 26. Preferably, the amount associated with the correction bolus 50 is independent of the partitioning of the slider path 54 with the slider position 42 between the first slider end position 56 and the second slider end position 58. Thus, the correction bolus 50 is preferably independent of the position 42 of the slider 40 and may be displayed in numerical values. In such a case, the updating via the slider position 42 only includes the first bolus amount of insulin 44 and the second bolus amount of insulin 46 when the position 42 of the slider 40 is changed by finger gestures, and leaves the correction bolus 50 at a fixed amount associated with the first amount of insulin 44 to be delivered immediately.

As illustrated in FIGS. 3a-3c, the first bolus amount of insulin 44 to be delivered immediately and a second bolus amount of insulin 46 to be delivered at a later point in time are arranged on the touch screen display 26 in connection with the respective slider end positions 56, 58 and may be displayed in percentages. Additionally, the correction bolus 50 may be displayed as separate item, e.g., separate from the first bolus amount of insulin 44 and in the vicinity of the first slider position 56 and may be displayed as a numerical value.

Figure 4:
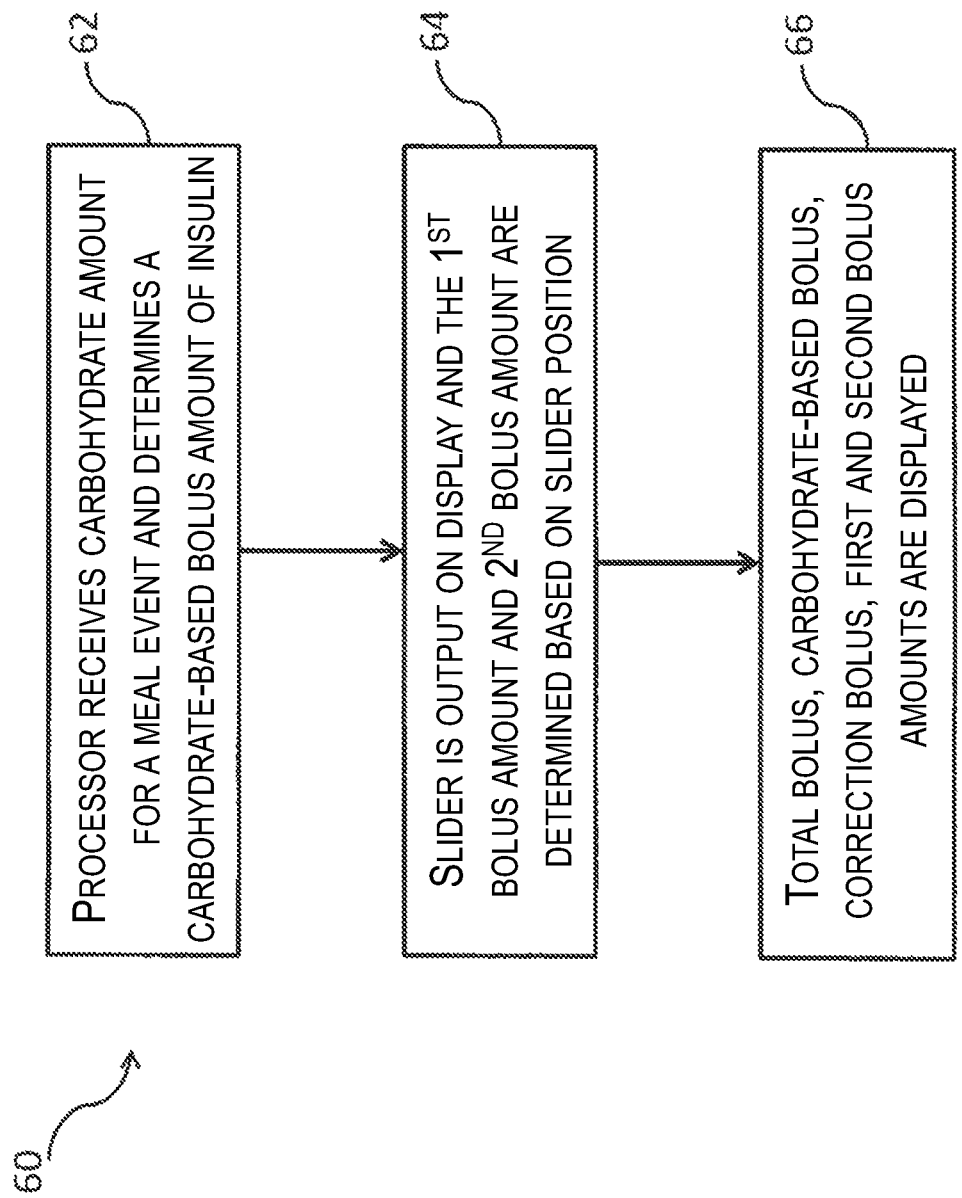
FIG. 4 shows an exemplary flow chart for adjusting the bolus amount of insulin through a slider.

FIG. 4 shows an exemplary flow chart 60 for adjusting the bolus amount of insulin through a slider 40.

According to this disclosure, the method for adjusting a bolus amount of insulin for a meal event 32 uses a control unit having a processor 28 and a touch screen display 26. In step 62, the processor 28 receives the carbohydrate amount associated with the meal event 32 and determines a carbohydrate-based bolus amount of insulin.

In step 64, the slider, movable via touch screen gestures, is output on the touch screen display 26, wherein the processor 28 determines, based on the position 42 of the slider 40, a first bolus amount of insulin 44 to be delivered immediately and/or a second bolus amount of insulin 46 to be delivered at a later point in time, wherein the first bolus amount of insulin 44 and/or the second bolus amount of insulin 46 add up to a carbohydrate-based bolus amount of insulin.

In step 66, the total meal bolus amount of insulin 48, including the carbohydrate-based bolus amount of insulin and/or a correction bolus 50, the correction bolus 50, the first bolus amount of insulin 44 to be delivered immediately, as determined by the position 42 of the slider 40 and a second bolus amount of insulin 46 to be delivered at a later point in time, as determined by the position 42 of the slider 40 are output or displayed on the touch screen display 26.

Figure 5:
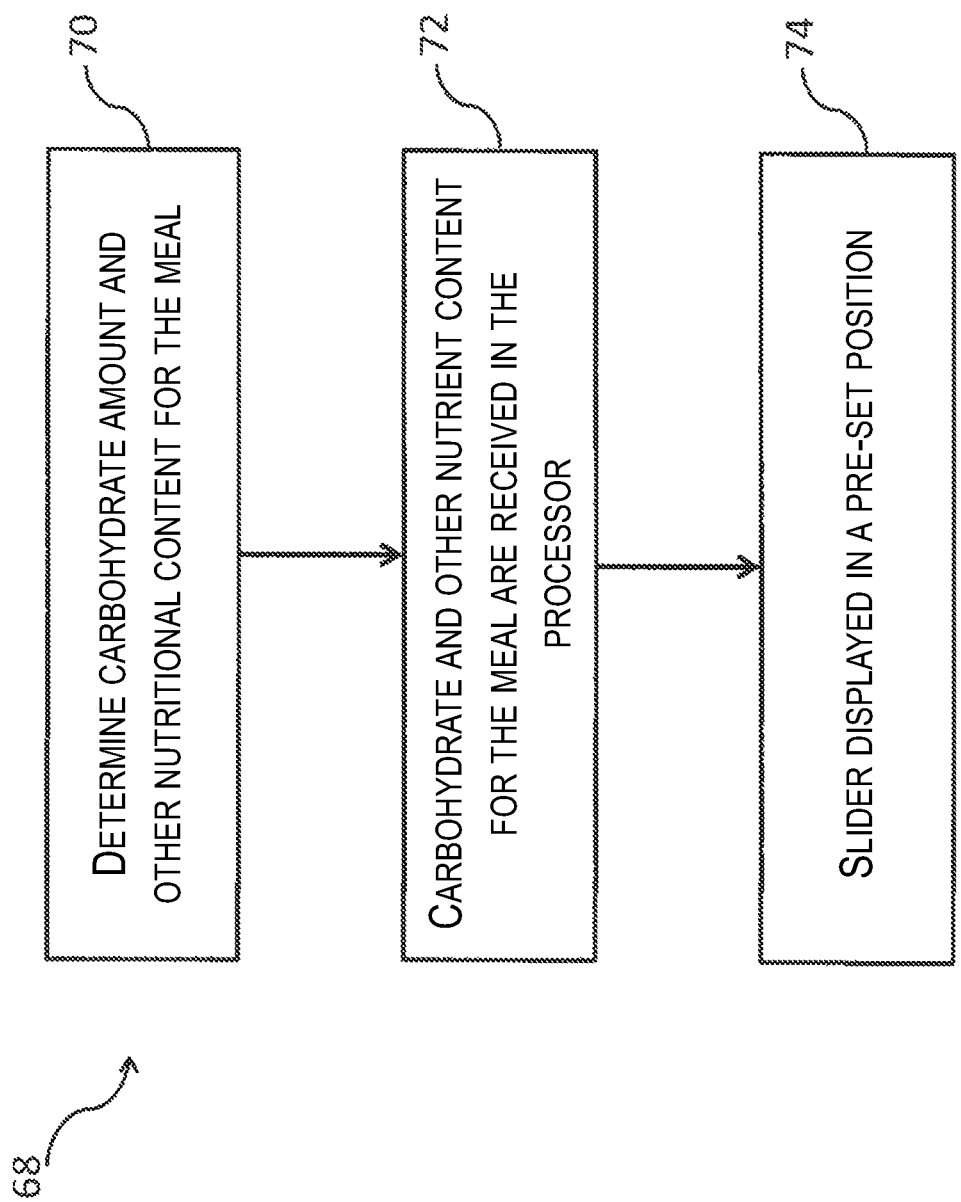
FIG. 5 shows a further exemplary flow chart for outputting a pre-set slider position for the carbohydrate-based bolus amount of insulin.

FIG. 5 shows a further exemplary flow chart 68 for outputting a pre-set slider position 42 for the carbohydrate-based bolus amount of insulin.

In order to more accurately predict the carbohydrate-based bolus amount of insulin and, in particular, the partitioning between the first bolus amount of insulin 44 to be delivered immediately and a second bolus amount of insulin 46 to be delivered at a later point in time, carbohydrate content and/or further nutrient content information associated with the meal event 32 are received by the processor 28 in step 72.

In order to do so, the preceding step 70 may include determining the carbohydrate amount and/or further nutrient meal content information via a food data base, including an estimated carbohydrate amount and/or further nutrient meal content information for specific meals or meal items. Alternatively or additionally, the carbohydrate amount and/or further nutrient meal content information may be determined by photographic reconstruction routines based on a photographic image of the meal or meal items provided by a camera unit of the medical control device 12.

In step 74, the slider 40 may be output with the displayed position 42 of the slider 40 being pre-set based on the provided carbohydrate amount and/or further nutrient meal content information. Such pre-setting results from the estimation of the carbohydrate amount and/or further nutrient meal content information via a food data base or photographic reconstruction routines and is used to determine the carbohydrate-based bolus amount, including first and second bolus amount 44, 46 and the respective delivery scheme timings.

FIGS. 6a-6d and FIGS. 7a-7c show exemplary embodiments for insulin pump and insulin pen based delivery schemes.

The carbohydrate-based bolus amount of insulin may be calculated according to an insulin delivery scheme, examples of which are shown in FIGS. 6a-6d and FIGS. 7a-7c, where the bolus amounts are only illustrated on a time scale schematically and without the heights having any reference to the actual amounts.

FIGS. 6a-6d illustrate exemplary delivery schemes as preferred for insulin pens 22. Such insulin delivery schemes may include the first bolus amount of insulin 44 to be delivered immediately and the correction bolus 50, as shown in FIG. 6a. The example of FIG. 6b includes the first bolus amount of insulin 44 to be delivered immediately and the correction bolus 50 to be delivered immediately and the second bolus amount of insulin 46 to be delivered at one discrete point later in time. The example of FIG. 6c includes the correction bolus 50 to be delivered immediately as well as the second bolus amount of insulin 46 to be delivered at one discrete point later in time. The example of FIG. 6d includes the first bolus amount of insulin 44 to be delivered immediately and the correction bolus 50 to be delivered immediately, as well as the second bolus amount of insulin 46 to be delivered in multiple parts at discrete points later in time.

FIGS. 7a-c illustrate exemplary delivery schemes as preferred for insulin pumps 18. Such insulin delivery schemes may include the first bolus amount of insulin 44 to be delivered immediately and the correction bolus 50 to be delivered immediately as shown in FIG. 7a. The example of FIG. 7b includes the first bolus amount of insulin 44 to be delivered immediately and the correction bolus 50 to be delivered immediately as well as the second bolus amount of insulin 46 to be delivered continuously at a constant rate starting at a later point later in time than the immediate boli 44, 50. The example of FIG. 7c includes the first bolus amount of insulin 44 to be delivered immediately and the correction bolus 50 to be delivered immediately as well as the second bolus amount of insulin 46 to be delivered according to a profile, shown here as an exemplary linear profile, continuously starting directly after the immediate boli 44, 50.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

The invention claimed is:

1. Method for adjusting a bolus amount of insulin for a meal event using a medical control device having a having a processor and a touch screen display, the method comprising the steps:

receiving with the processor, a carbohydrate amount associated with the meal event and determining a carbohydrate-based bolus amount of insulin;

outputting on the touch screen display a slider movable via touch screen gestures, wherein the processor determines, based on a position of the slider, a first bolus amount of insulin to be delivered at a first point in time and a second bolus amount of insulin to be delivered at a later point in time, wherein the first bolus amount of insulin and the second bolus amount of insulin add up to the carbohydrate-based bolus amount of insulin, outputting on the touch screen display a total meal bolus amount of insulin including the carbohydrate-based bolus amount of insulin and a correction bolus, further outputting on the touch screen display the correction bolus, the first bolus amount of insulin and the second bolus amount of insulin;

receiving, with the medical control device, a measured glucose level which was measured prior to the meal event, providing the measured glucose level to the processor and determining with the processor, the correction bolus based on the measured glucose level, wherein the correction bolus, the first bolus amount of insulin and the second bolus amount of insulin add up to the total meal bolus amount of insulin;

wherein the step of outputting on the touch screen display further comprises outputting the correction bolus, wherein the correction bolus is delivered with the first bolus at the first point in time and independently of the position of the slider; and wherein further nutrient meal content information associated with the meal event is received by the processor and is used together with the carbohydrate amount associated with the meal event to determine the carbohydrate-based bolus amount of insulin and an initial displayed position of the slider is pre-set based on the carbohydrate amount associated with the meal event and/or the further nutrient meal content information associated with the meal event.

2. The method of claim 1 wherein the carbohydrate amount and/or further nutrient meal content information is determined via a food data base including an estimated carbohydrate amount and/or further nutrient meal content information for specific meals or meal items.

3. The method of claim 2 wherein the carbohydrate amount and/or further nutrient meal content information is determined by photographic reconstruction routines based on a photographic image of the meal or meal items provided by a camera coupled with the medical control device.

4. The method of claim 1 wherein the touch screen display includes sensors for detecting finger gestures along a slider path reaching from a first slider position to a second slider position, wherein the first slider position is associated with the carbohydrate-based bolus amount of insulin being the first bolus amount of insulin and the second slider position is associated with the carbohydrate-based bolus amount of insulin being the second bolus amount of insulin.

5. The method of claim 4, wherein the position of the slider between the first slider position and the second slider position is associated with the first bolus amount of insulin and the second bolus amount of insulin, wherein the partitioning between first and second bolus amount of insulin is determined based on the partitioning of the slider path by the position of the slider position between the first slider position and the second slider position.

6. A medical control device for adjusting a bolus amount of insulin on a meal event, wherein the device includes:
a processor adapted to receive a carbohydrate amount associated with the meal event and further nutrient meal content information associated with the meal event and wherein the processor is further adapted to use the carbohydrate amount associated with the meal event together with the further nutrient meal content information associated with the meal event to determine a carbohydrate-based bolus amount of insulin;
a touch screen display which displays a slider movable via touch screen gestures, wherein the processor determines, based on a position of the slider, a first bolus amount of insulin to be delivered at a first point in time and a second bolus amount of insulin to be delivered at a later point in time, wherein the first bolus amount of insulin and the second bolus amount of insulin add up to a carbohydrate-based bolus amount of insulin;
the touch screen display further displaying a total meal bolus amount of insulin including the carbohydrate-based bolus amount of insulin and a correction bolus, the touch screen display displaying the correction bolus, the first bolus amount of insulin and the second bolus amount of insulin;
wherein the medical control device is configured to receive a measured glucose level which was measured prior to the meal event, and provide the measured glucose level to the processor and the processor is configured to determine the correction bolus based on the measured glucose level, and wherein the correction bolus, the first bolus amount of insulin and the second bolus amount of insulin add up to a total meal amount of insulin;
wherein the touch screen display further displays the correction bolus, wherein the correction bolus is delivered with the first bolus at the first point in time and independently of the position of the slider; and
wherein an initial displayed position of the slider is pre-set based on the carbohydrate amount associated with the meal event and/or the further nutrient meal content information associated with the meal event.

7. The medical control device according to claim 6 wherein the medical control device communicates with at least one medical device and/or a cloud server.

8. The medical control device according to claim 6 wherein the medical control device is configured to communicate the total meal amount of insulin, the first bolus amount of insulin and the second bolus amount of insulin to an insulin delivery system.

9. A computer program product stored on a nontransitory computer readable storage medium wherein the computer program product configures a processor to execute the method of claim 1 in combination with a touch screen display.

10. The medical control device according to claim 6 wherein the touch screen display displays the first bolus amount in close vicinity to a first slider end position, the second bolus amount in close vicinity to a second slider end position and the correction bolus as a separate item in vicinity of the first slider end position.

11. The medical control device according to claim 6 wherein the first bolus amount and the second bolus amount are displayed in percentages and the total meal bolus amount and the correction bolus are displayed as numerical values of amounts of insulin.

12. The method of claim 5 wherein the touch screen display displays the first bolus amount in close vicinity to the first slider position, the second bolus amount in close vicinity to the second slider position and the correction bolus as a separate item in vicinity of the first slider position.

13. The method of claim 5 wherein the first bolus amount and the second bolus amount are displayed in percentages and the total meal bolus amount and the correction bolus are displayed as numerical values of amounts of insulin.

14. The method of claim 1 determining an insulin delivery scheme for the second bolus amount of insulin based upon a delivery device for the second bolus amount of insulin wherein the second bolus amount of insulin is delivered continuously over a time range when the delivery device is an insulin pump and the second bolus amount of insulin is delivered in one or more discrete parts at discrete points of time when the delivery device is an injection pen.

15. The method of claim 14 wherein the medical control device automatically detects what type of delivery device is connected to the medical control device when determining the insulin deliver scheme for the second bolus amount of insulin.

* * * * *